United States Patent [19]

Quame

[11] 4,134,730
[45] Jan. 16, 1979

[54] SPOTTING SYSTEMS AND METHODS PERTAINING THERETO

[76] Inventor: Babington A. Quame, 331 E. 29th St., New York, N.Y. 10016

[21] Appl. No.: 835,168

[22] Filed: Sep. 20, 1977

[51] Int. Cl.² .................. G01N 33/16; G01N 1/14
[52] U.S. Cl. .................. 23/230 B; 73/425.4 P; 73/425.6; 422/100
[58] Field of Search .................. 23/259, 253 R, 230 R, 23/230 B; 73/425.6, 425.4 P; 141/130

[56] References Cited

U.S. PATENT DOCUMENTS

| | | | |
|---|---|---|---|
| 3,285,296 | 11/1966 | Ishimaru et al. | 73/425.6 |
| 3,640,388 | 2/1972 | Ferrari | 73/425.6 |
| 3,667,917 | 6/1972 | Brandt | 23/253 X |
| 3,748,909 | 7/1973 | Kuo | 73/425.4 P |
| 3,758,275 | 9/1973 | Quame | 23/253 X |
| 3,843,323 | 10/1974 | Quame | 23/253 X |
| 3,995,496 | 12/1976 | Bickford | 73/425.6 |

*Primary Examiner*—R.E. Serwin
*Attorney, Agent, or Firm*—Steinberg & Blake

[57] ABSTRACT

In order to achieve a specimen in the form of a dry spot on a given surface, use is made of an elongated capillary tube one end region of which communicates fluid-tightly with the interior of a flexible resilient enclosure in the form of a suitable bulb which after being compressed will by itself expand to its initial volume, this bulb in turn communicating fluid-tightly with the interior of a container which is provided in its interior with an air-flow retarding material capable of regulating the flow of air resulting from compression and subsequent expansion of the flexible resilient enclosure in such a way that when the end of the capillary tube distant from the enclosure is placed in a solution of the specimen and the enclosure after being compressed is permitted to expand, the solution will be drawn into the capillary tube and will be held therein while the lower end of the capillary tube is placed near a surface onto which, as a result of the condition of the air in the interior of the resilient enclosure, the solution will flow in its entirety out of the capillary tube so that after drying the solution thus deposited on the surface will form the desired spot thereon.

25 Claims, 3 Drawing Figures

SPOTTING SYSTEMS AND METHODS PERTAINING THERETO

BACKGROUND OF THE INVENTION

The present invention relates to spotting systems and methods pertaining thereto.

Thus, the present invention relates to thin-layer chromatography (TLC) according to which specimens in the form of spots are provided on a suitable precoated thin-layer chromatographic plate or paper.

As is well known, procedures in connection with TLC are utilized for purposes of testing samples such as urine samples.

Conventional procedures of this general type suffer from a number of drawbacks. Thus, there are unavoidable inaccuracies inherent therein, and in addition they are time-consuming and expensive.

According to conventional procedures a dried specimen in the bottom of a beaker has a given amount of solvent added thereto in order to form a solution therefrom, and then at least part of this solution is transferred to a chromatographic paper or plate in order to form a spot thereon. These procedures conventionally require a number of transfer operations during which part of the solution in the beaker is transferred to the chromatographic sheet material, with one quantity of liquid which is deposited on the latter sheet material having additional quantities of liquid added thereto in order to form a spot on the sheet material when the liquid solution deposited thereon dries. During the several transfer operations utilized in connection with providing a single spot, the solution in the beaker continues to evaporate so that the concentration of the solution changes in an uncontrollable manner, so that as a result there are unavoidable inaccuracies inherent in such conventional procedures.

In addition, a number of spots are conventionally provided on a single layer of chromatographic sheet material, and because the deposited liquid for a given spot spreads it is not uncommon for adjacent spots to run into each other, thus creating further inaccuracies.

Moreover, the costs involved in such procedures, particularly the labor costs, render such conventional procedures undesirably expensive.

Attempts have already been made to alleviate the problems inherent in conventional procedures of the above type, and in this connection reference may be made to applicant's earlier U.S. Pat. Nos. 3,758,275 and 3,843,323 which do indeed disclose how it is possible to improve the procedures set forth above. The present invention relates to a further improvement over the above conventional procedures.

SUMMARY OF THE INVENTION

It is accordingly a primary object of the present invention to provide systems and methods which make it possible to achieve specimens in the form of spots, according to TLC techniques, in a highly accurate manner while at the same time requiring far less costs than conventional procedures.

A more specific object of the present invention is to provide methods and apparatus according to which it becomes possible in a single operation to deposit on a chromatographic sheet material a quantity of specimen solution which is sufficient to provide the required spot, upon drying, while at the same time reliably preventing running of a plurality of spots into each other.

Yet another object of the present invention is to provide not only low-cost devices to be utilized in connection with procedures as set forth above, but also highly effective methods for manufacturing such devices.

According to the invention a device utilized for depositing a given quantity of specimen solution onto a chromatographic sheet material includes an elongated capillary tube which is open at both of its opposed ends, this tube being fluid-tightly connected at one of its ends to a resilient, flexible enclosure means, in the form of a suitable hollow bulb which can be compressed by the operator and which, when released by the operator, will automatically expand back to its initial volume, so that in this way it is possible to suck a solution specimen from a beaker into the capillary tube. The interior volume of the capillary tube is only slightly greater than the volume of the specimen solution required to form a single spot. The resilient flexible enclosure means also communicates fluid-tightly with the interior of a container so that air can flow between the interior of the flexible resilient enclosure means and the interior of the container. In the interior of this container there is situated an air-flow retarding means preferably in the form of a suitable fibrous material which is compressed into the interior of the container. Thus, this container and the material therein form an air-flow control means cooperating with the flexible resilient enclosure means in such a way that when the latter is compressed and then released to cause a specimen solution to be sucked into the capillary tube, this specimen solution will be retained in the capillary tube, while on the other hand when the end of the capillary tube distant from the flexible resilient enclosure means is placed close to a chromatographic sheet material, the solution in the capillary tube will automatically flow out of the latter onto the sheet material to be deposited and subsequently dried thereon so as to form the required spot which can be subsequently analyzed in a well known manner.

BRIEF DESCRIPTION OF DRAWINGS

The invention is illustrated by way of example in the accompanying drawings which form part of this application and in which.

DESCRIPTION OF PREFERRED EMBODIMENTS

Figure 1:
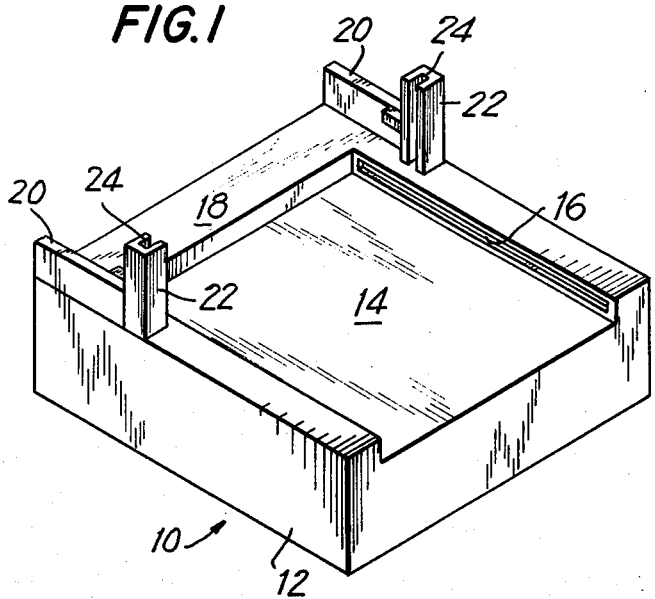
FIG. 1 is a schematic perspective illustration of a support means utilized in connection with the invention.

Referring now to the drawings, there is schematically illustrated in FIG. 1 a support means 10 for supporting various components utilized in connection with the present invention. This support means 10 is in the form of a hollow box-like structure 12 having a depressed surface 14 on which the chromatographic sheet material is placed. In the interior of the structure 12 there are components such as heating elements and a fan, so that in this way it is possible for hot air to stream out of one or more slots such as the slot 16 to flow over the chromatographic sheet material so as to dry the liquid solutions deposited thereon. In this connection reference may be made to applicant's earlier U.S. Pat. No. 3,758,275.

The upper surface 18 of the support means 10 fixedly carries suitable brackets 20 which in turn serve to fix to the top surface 18 upright guide members 22. These guide members 22 are respectively formed with upright grooves 24 which face each other and are located in a common plane.

Figure 2:
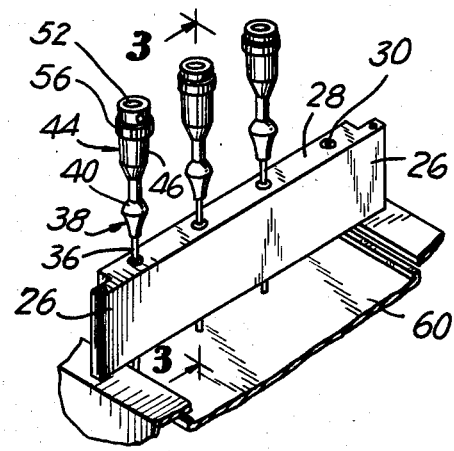
FIG. 2 is a schematic fragmentary perspective illustration of the structure of the invention used in connection with depositing spot-forming quantities of liquid solution onto chromatographic sheet material.

Referring to FIG. 2, it will be seen that the grooves 24 are adpated to receive tongues 26 formed at the opposed ends of a carrier means 28 in the form of a suitable plate which may be made of any wood, metal, or other rigid material such as a plastic material. The guides 22 are omitted from FIG. 2 for the sake of clarity. The tongues 26 are simply slipped downwardly along the grooves 24 so that in this way the carrier means 28 can be mounted on the support means 10 to assume the position indicated in FIG. 2.

Figure 3:
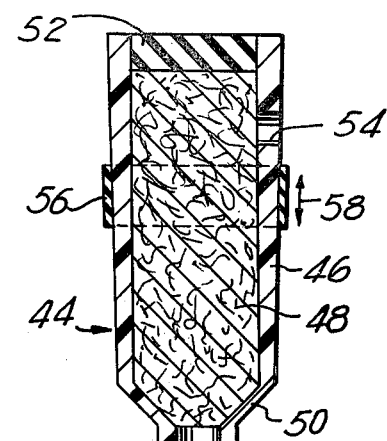
FIG. 3 is a partly fragmentary sectional elevation taken along line 3—3 of FIG. 2 in the direction of the arrows and showing at a scale which is enlarged as compared to FIG. 2 the details of the structure of the invention.
Figure 3:
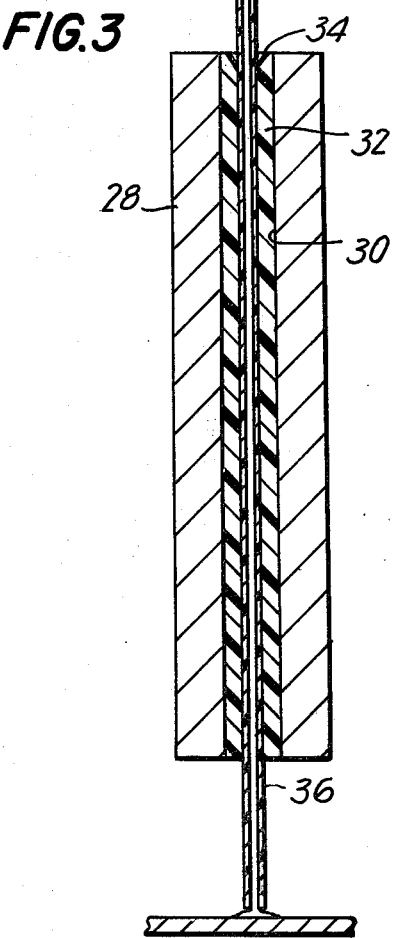

The carrier plate 28 is formed with a number of bores 30 which are vertical in the manner apparent from FIG. 3 so that each bore 30 extends from the top surface of the carrier plate 28 to the bottom surface thereof at a location adjacent the surface 14. In each of the bores 30 there is a plastic sleeve 32 made, for example, of a material such as polyethylene, and the sleeve 32 itself has an interior bore passing therethrough and being tapered at its upper end region 34 so as to facilitate introduction into the sleeve 32 of a capillary tube 36. The capillary tube 36 while slidable through the guide sleeve 32 nevertheless has sufficient frictional engagement therewith to be maintained in the tube 32 in the manner apparent from FIGS. 2 and 3.

The capillary tube 36 may be made of plastic, glass, or even stainless steel. Straight lengths of glass tubing of relatively small diameter are preferred for the capillary tubes 36 because such capillary tubes are extremely inexpensive.

As is apparent from FIG. 3, the capillary tube 36 is open at its opposed ends. At the region of its upper end the capillary tube is fluid-tightly connected with a flexible resilient enclosure means 38 in the form of a bulb 40 of rubber or other suitable resilient flexible plastic. The bulb 40 can readily be compressed between the fingers of the operator and when released will automatically expand back to the condition thereof shown in FIG. 3. At its lower end the bulb 40 has a wall 42 formed with an opening passing therethrough for frictionally receiving the upper end region of the capillary tube 36 which thus remains connected in a fluid-tight manner with the bulb 40, communicating with the interior thereof. It is to be noted that the wall 42 and the bore therethrough are such that it is a simple matter quickly and conveniently to remove one capillary tube 36 and introduce another capillary tube 36 through the bore in the wall 42 so as to assume with respect to the bulb 40 the condition illustrated in FIG. 3.

The interior of the flexible resilient enclosure means 38 also communicates fluid-tightly with an air-flow control means 44. This means 44 includes a container 46 made of a suitable plastic and having a lower end extending fluid-tightly into the interior of the bulb 40 in the manner apparent from FIG. 3. Thus the upper end of the bulb 40, as viewed in FIG. 3, is formed with an opening into which the lower end of the container 46 is placed with the edge which defines the upper opening of the bulb 40 being stretched to some extent in order to surround the lower end region of the container 46 so as to achieve in this way the fluid-tight connection between the container 46 and the bulb 40, and this connection can be permanently maintained.

As is apparent from FIG. 3, the lower end of the container 46 is formed with an axial bore so as to provide communication between the interior of the container 46 and the interior of the bulb 40. The interior of the container 46 also carries a means for controlling the flow of air between the bulb 40 and the container 46, this latter means being an air-flow retarding means 48 preferably in the form of cotton wadding treated as described below and compressed into the interior of the container 46 in the manner apparent in FIG. 3.

The air-flow retarding means 48 can take many different forms. For example it may include materials such as glass wool or even opposed end layers of glass wool between which a powdered granular material such as sand, for example, is located. However it has been found from experience that the most preferable form for the means 48 is a body of simple cotton wadding, forming a fibrous material which is compressed into the interior of the container 46, against the shoulder 50 thereof, in the manner apparent from FIG. 3. The cotton wadding is impregnated with a wax-like substance for achieving in this way an ideal air-flow control. Thus the cotton wadding is preferably soaked in a solution formed from preferably one part of a silicone lubricant such as a high-vacuum grease, and three parts of a solvent which preferably is benzene. After the cotton wadding has been thoroughly soaked by being placed in such solution, the cotton wadding is removed from the solution and permitted to dry, and the resulting fibrous material has proved to be ideal for the purposes of the present invention. A quantity of this fibrous material is compressed into the container 46 in the manner apparent from FIG. 3 so as to form the means 48 which will create the desired type of air flow between the interiors of the container 46 and the enclosure means 38.

According to one method of the invention, after a quantity of the cotton wadding 48 is compressed into the container 46, the upper end of the container 46 is closed by way of a suitable plug 52 of rubber or similar elastomeric material. Thus a circular plug 52 is simply pressed into the top open end of the container 46 so as to fluid-tightly close the container 46. A side wall portion of the container 46 is also formed with an opening 54 passing therethrough. This opening 54 can be formed at any time such as before or after the cotton wadding 48 and plug 52 are applied to the container. The opening 54 is formed simply by pushing a suitable metal pin through the plastic material of the container 46.

In the illustrated example a means for adjusting the size of the opening 54 is provided. This means 56 takes the form of a simple sleeve in the form of a ring of plastic or other suitable sheet material which is freely slidable along the exterior of the container 46 in the manner shown by the double-headed arrow 58. Thus the sleeve 56 can be shifted so as to cover the opening 54 to a given extent, in a manner described in greater detail below.

It is also possible, however, according to a further feature of the invention, to provide a device which does not require the adjusting means 56. Thus, before the plug 52 is provided the above-described impregnated cotton wadding is compressed into the interior of the container 46. Then the bulb 40 is compressed while the lower end of the capillary tube 36 is placed in a liquid such as methyl alcohol. Then the bulb 40 is released so that it will tend to expand back to its original condition. If the bulb 40 expands back to its original condition very readily and the liquid such as methyl alcohol runs out of the tube 36, then it is known that the cotton wadding 48 has not been compressed sufficiently into the interior of the container 46. Thus if this liquid simply runs out of the capillary tube the operator will compress the cotton wadding 48 to a greater degree and will add additional cotton wadding if required. When the compression of the cotton wadding 48 is such that the liquid sucked into the capillary tube remains therein without any tendency to flow out, then it is known that the cotton wadding 48 has been properly situated in the interior of the container 46. Of course, if upon compression of the bulb 40 the latter cannot expand automatically back to its original condition it is known that the extent of compression of the cotton wadding is too great, and it is loosened to achieve the required condition according to which upon expansion of the bulb 40 the liquid will be sucked into the tube 36 and will be held therein. When the latter condition is obtained the plug 52 is applied and a simple hole is punched with a small pin in the side wall of the container 46, and now the device is completed and ready for use. Thus, with the device manufactured in this way it is unnecessary to provide the sleeve 56.

It is to be noted that the plastic guide tubes 32 which are introduced into and held in the bores 30 of the carrier plate 28 have an inner diameter corresponding to the outer diameter of the capillary tubes 36. Thus if capillary tubes of different sizes are used it is possible to replace the guide tubes 32 with other guide tubes which have corresponding inner diameters.

Furthermore, it is to be understood that although FIG. 2 illustrates a carrier means 28 capable of accommodating only four of the devices shown in FIG. 3, it is expedient and common that in practice a much greater number of devices will be accommodated by a single carrier means 28. Thus in practice the carrier plate 28 is usually constructed in such a way that it will accommodate ten of the devices shown in FIG. 3.

In practicing the method of the invention, use is made of beakers which have therein dried urine specimens. The manner in which such dried specimens are provided respectively in a number of beakers is disclosed, for example, in applicant's earlier U.S. Pat. No. 3,843,323. Into such a beaker which has a dried residue of urine specimen therein there is placed a predetermined quantity of solvent such as methanol. This predetermined quantity of solvent is just enough to form with the dried specimen a solution the volume of which is slightly less than the interior volume of the capillary tube 36. In one specific method carried out according to the invention it has been found from experience that it is only necessary to introduce into such a beaker two drops of methanol in which the dried specimen becomes thoroughly dissolved, and then the beaker is tilted so as to locate the solution at a lower corner of the beaker between the bottom and side wall thereof. Thus the beaker need only be tilted to an angle of approximately 45° with respect to a vertical axis, and the solution will conveniently be situated in a form in which it can readily be sucked into the capillary tube 36. For this purpose the bottom end of the capillary tube is introduced into the solution in the beaker, while the bulb 40 has been compressed and then the bulb 40 is released to expand so that the solution is entirely sucked out of the beaker into the capillary tube 36 almost filling the latter. Thus according to an important feature of the invention the solution which is sucked into the capillary tube 36 never reaches the bulb 40 so that the latter remains at all times uncontaminated by the solution.

If the device of the invention is manufactured according to the method described above where a test is preliminarily made with a liquid such as methyl alcohol, then, as was pointed out above, the adjusting device 56 is not required and upon release of the bulb 40 the solution is reliably sucked in its entirety from the beaker into the capillary tube. However, if the cotton wadding is simply compressed into the container and the hole 54 is punched through the wall thereof, without any preliminary testing, then the adjusting means 56 is provided. When such a device is initially used the bottom end of the capillary tube is introduced into the solution and after compression of the bulb 40 it is permitted to expand so as to suck the solution into the capillary tube. If it is found that the solution runs out of the capillary tube so that it cannot be held therein, the operator will slide the sleeve 56 so as to partly cover the opening 54, thus controlling the flow of air, and the solution will again be sucked into the tube 36. This adjustment of the tube 56 is provided so as to cover the opening 54 to such an extent that when the bulb 40 is released and the solution is sucked into the tube 36, the solution will be held therein. At this time it is known that the adjusting means 56 has been properly adjusted, and can then simply remain in its adjusted position during many successive uses of the structure of the invention in the manner described below.

After a capillary tube 36 has thus been provided with an amount of specimen solution which almost fills the capillary tube 36 and is held therein, this capillary tube 36 is placed through one of the sleeves 32 of the carrier plate 28. The capillary tube 36 is displaced axially through the sleeve 32 until the bottom end of the capillary tube 36 almost engages the chromatographic sheet material 60 which is schematically illustrated in FIG. 2 situated on the depressed surface 14 of the support means 10. As soon as the lower end of the tube 36 is near to the sheet material 60, the liquid solution at the lower end of the tube 36 comes in contact with the material 60 and due to the nature of the chromatographic sheet material which is absorbent, the liquid solution in the capillary tube 36 flows out of the latter as a result of the surface tension of the liquid. Thus the liquid simply flows automatically out of the tube 36 onto the sheet material 60. An extremely short time is required for this purpose. It is to be noted that the stiffness of the bulb 40 and the weight of the container 46 and materials carried thereby are such that the entire structure remains in the upright attitude shown in FIG. 3. Thus the container 46 and the parts carried thereby are sufficiently light so that there is no tendency for this structure to cause the bulb 40 to bend even if the center of gravity of the container 46 and the parts carried thereby is not precisely in line with tube 36. It has been found from experience that this structure remains upright by itself in a manner shown in FIG. 3.

Thus, the above procedures are repeated with each of the devices shown in FIG. 3, and a series of these devices are situated one after the other in the openings of the guide sleeves 32 carried by the carrier means 28, so that, for example, a series of ten spots are rapidly and effectively formed on the chromatographic sheet material 60. By the time the last device has been placed on the carrier means 28 the liquid solution has been completely emptied from the first device mounted thereon, and after a period of no more than two minutes subsequent to mounting of the last device of FIG. 3 on the carrier means 28 it is possible to remove the latter and all of the devices carried thereby, and the above operations can be repeated with another sheet of chromatographic sheet material with another carrier 28 and with additional devices having the structure shown in FIG. 3 or the structure which does not require the adjusting means 56, as pointed out above. Of course the air flowing through the slots 16 rapidly dries the liquid so as to form dry spots very rapidly on the chromatographic sheet material 60.

As soon as the above operations have been completed with one carrier means 28, the devices of the invention are removed therefrom. Then the several tubes 36 are removed from the bulb 40 and discarded, and new perfectly clean tubes 36 are introduced through the openings in the walls 42 of the bulbs 40 in the manner described above, so that now a completely new series of devices are ready for use, and because of the low cost of the discarded tubes 36, the entire procedure required by the invention is exceedingly inexpensive while at the same time highly accurate and reliable.

What is claimed is:

1. In a system for depositing on a given surface at least one predetermined quantity of a liquid from which a spot will form on said surface, an elongated capillary tube having opposed open ends, flexible, resilient enclosure means fluid-tightly connected with said capillary tube at the region of one of said ends thereof and having a hollow interior communicating with the interior of said capillary tube through said one open end thereof, and air-flow control means fluid-tightly connected with said enclosure means and communicating with the interior thereof for controlling the flow of air into and out of said enclosure means upon compression and expansion thereof, said air-flow control means and enclosure means cooperating with each other and said capillary tube for sucking said predetermined quantity of liquid into said capillary tube and holding said predetermined quantity of liquid in said tube after said enclosure means is compressed with the other of said open ends of said tube then being introduced into said given quantity of liquid, whereupon said enclosure means is released to expand and suck the given quantity of liquid into the capillary tube, said liquid in the capillary tube then being held therein until the other end thereof is placed in proximity to said surface whereupon the liquid in the capillary tube will flow out of the same onto the surface while the interior of said enclosure means communicates with the outer atmosphere through said air-flow control means, said enclosure means being in the form of a hollow bulb made of a resilient flexible sheet material which after being compressed will automatically expand, and said air-flow control means including a container fluid-tightly connected with said bulb and having a hollow interior communicating with the interior of said bulb and capable of communicating with said capillary tube only through said bulb, the latter being situated between said capillary tube and said container, said container being formed distant from said bulb with at least one opening through which the interior of said container communicates with the outer atmosphere, and said container having in its interior between said opening and said bulb a means for creating a given resistance to air flow between said opening and said bulb.

2. The combination of claim 1 and wherein said means for creating said resistance to air flow includes a body of fibrous material compressed in the interior of said container and situated at least in part between said opening thereof and said bulb.

3. The combination of claim 2 and wherein said fibrous material includes cotton wadding.

4. The combination of claim 3 and wherein said cotton wadding is impregnated with a material which contributes to the resistance to air flow created by the cotton wadding.

5. The combination of claim 4 and wherein said material impregnated in the cotton wadding includes a silicone lubricant such as a high vacuum grease.

6. The combination of claim 1 and wherein said capillary tube is straight.

7. The combination of claim 1 and wherein the length and inner diameter of the capillary tube provide the latter with an interior volume at least slightly greater than the volume occupied by said predetermined quantity of liquid so that the latter can be sucked into said tube without entering into said enclosure means.

8. The combination of claim 9 and wherein said enclosure means is removably connected with said capillary tube, so that after the liquid initially situated in said capillary tube flows out of the latter, said capillary tube can be removed from said enclosure means and replaced by another capillary tube, with the liquid being maintained out of contact with the enclosure means so that the latter does not become contaminated by liquid sucked into the capillary tube.

9. The combination of claim 1 and wherein said container carries and adjusting means for adjusting the size of said opening to control the flow of air in the interior of said container.

10. The combination of claim 9 and wherein said adjusting means includes an annular member slidable on said container for covering said opening to a selected extent.

11. The combination of claim 1 and wherein said container is provided with a plug for closing the interior of the container after the means creating the resistance to air flow is situated therein.

12. The combination of claim 1 and wherein when said other end of said capillary tube is place in proximity to said surface said enclosure means extends upwardly from said capillary tube and said air-flow control means extends upwardly from said enclosure means, said capillary tube being substantially straight and said enclosure means having a sufficient stiffness while said air-flow control means is of a sufficiently light weight to enable said enclosure means to carry said air-flow control means with the latter and said enclosure means extending substantially along a straight line along which said capillary tube extends.

13. The combination of claim 1 and wherein the system includes a support means for supporting a sheet material having the surface onto which the liquid is to be deposited, said capillary tube, enclosure means, and air-flow control means forming one of a plurality of units each of which includes said capillary tube, enclosure means, and air-flow control means, and carrier means for carrying a plurality of said units, said carrier means being supported also by said support means and carrying said plurality of units with said other ends of said capillary tubes thereof situated in proximity to said surface of the sheet material.

14. The combination of claim 13 and wherein said carrier means is removably connected with said support means.

15. The combination of claim 13 and wherein said carrier means includes a plate formed with a plurality of openings through which the capillary tubes of said units extend.

16. The combination of claim 15 and wherein said plate has in said openings thereof plastic sleeves respectively formed with bores through which said capillary tubes extend.

17. A method for manufacturing a capillary device to be used for depositing a given quantity of liquid on a given surface, the device having a capillary tube, a resilient flexible enclosure connected to the capillary tube at one end region thereof and communicating with the interior of said capillary tube, and a container connected to the enclosure at a region thereof distant from said capillary tube, so that said flexible enclosure is between said container and capillary tube, and said container having a hollow interior communicating with the interior of said flexible enclosure and capable of communicating with said capillary tube only through said flexible enclosure, said container having distant from said flexible enclosure an opening through which said container communicates with the outer atmosphere, the improvement comprising the step of introducing into the container a material which will create a resistance to flow of air therein upon compression and expansion of said flexible enclosure.

18. A method as recited in claim 17 and wherein the material introduced into the container is a fibrous material which is compressed into the container.

19. A method as recited in claim 18 and wherein the fibrous material is cotton wadding impregnated with a waxlike substance.

20. A method as recited in claim 19 and wherein the cotton wadding before being compressed into the container is soaked in a solution of a silicone lubricant and benzene, is then removed from the solution and dried, and is then compressed into the container.

21. A method as recited in claim 20 and wherein the solution includes one part of silicone lubricant to three parts of benzene.

22. A method as recited in claim 21 and wherein after the material is compressed into the container the enclosure is compressed and the capillary tube is introduced into a liquid such as methyl alcohol to suck a given quantity thereof into the capillary tube when the enclosure is released so as to be permitted to expand, and the compression of the material being adjusted so that the liquid sucked into the capillary tube will be held therein, then closing the container and forming said opening in a side wall thereof, the latter steps being performed in any sequence.

23. A method as recited in claim 22 and wherein a resilient plug is applied to the container at an open end thereof spaced from said opening for closing the container at the open end thereof.

24. A method for providing spots of specimens on a surface, comprising the steps of dropping two drops of methanol into a beaker which has a dried urine residue therein, for dissolving the residue in the drops of methanol, then sucking the drops of methanol with the urine residue dissolved therein into a capillary tube, and then placing an end of the capillary tube close to a surface onto which the liquid in the capillary tube flows from the interior of the capillary tube.

25. A method of providing on a given surface a specimen spot, comprising the steps of adding to the residue of a specimen in a beaker only an amount of solvent sufficient to dissolve the residue and form a single spot therefrom, sucking the thus-formed solution in its entirety into a capillary tube the interior volume of which is at least slightly greater than the total volume required for said solution which is sucked out of the beaker, and placing a lower end of the capillary tube with the solution in the latter sufficiently close to said surface for the solution in the capillary tube to flow in its entirety onto said surface to form a spot after drying on said surface.

* * * * *